US00PP15538P3

(12) United States Plant Patent
Ilsink

(10) Patent No.: US PP15,538 P3
(45) Date of Patent: Feb. 8, 2005

(54) HYBRID TEA ROSE PLANT NAMED 'INTERYASSOR'

(50) Latin Name: *Rosa hybrida*
Varietal Denomination: Interyassor

(75) Inventor: Peter Ilsink, Doorn (NL)

(73) Assignee: Interplant B.V., International Plant and Trading (NL)

( * ) Notice: Subject to any disclaimer, the term of this patent is extended or adjusted under 35 U.S.C. 154(b) by 0 days.

(21) Appl. No.: 10/683,594

(22) Filed: Oct. 9, 2003

(65) Prior Publication Data

US 2004/0078855 P1 Apr. 22, 2004

(51) Int. Cl.[7] ..... A01H 5/00

(52) U.S. Cl. ..... Plt./139

(58) Field of Search ..... Plt./139, 140

(56) References Cited

PUBLICATIONS

UPOV–ROM GTITM, Plant Variety Database, 2003/05, GTI Jouve Retrieval Software, Citation for Rosa 'Interyassor'.*

* cited by examiner

*Primary Examiner*—Anne Marie Grunberg
*Assistant Examiner*—June Hwu
(74) *Attorney, Agent, or Firm*—Klarquist Sparkman LLP

(57) ABSTRACT

Hybrid tea rose plant having big full flower, thornless stem, very shiny leaves and excellent vase life.

1 Drawing Sheet

Genus and species: *Rosa hybrida.*
Variety denomination: Interyassor.

SUMMARY OF THE INVENTION

The present invention relates to a new and distinct variety of hybrid tea rose plant named 'Interyassor' which was originated by me by crossing an unnamed seedling with an unnamed seedling.

BACKGROUND OF THE INVENTION

The primary objective of this breeding was to produce a new rose variety having the large headed dark red productive hybrid tea rose.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Big full flower;
2. Thornless stem;
3. Very shiny leaves; and
4. Excellent vase life.

Asexual reproduction of this new variety by grafting on 'Natal Briar' understock (unpatented), as performed at Watsonville, Calif., shows that the foregoing and all other characteristics and distinctions come true to form and are established and transmitted through succeeding propagations.

Comparison with Parent

'Interyassor' has its nice smooth stem from its seed parent and the nice big flower from its pollen parent.

Comparison with Similar Variety

'Interyassor' is different from the similar varieties 'Passion First Red' (not patented) and 'Red Berlin' (not patented) because of its shiny foliage and the smooth stems.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (1996), except where ordinary dictionary significance of color is indicated.

Parentage:
*Seed parent.*—Unnamed seedling.
*Pollen parent.*—Unnamed seedling.

FLOWER

Observations made from plants which were about nine months old and which were grown in a greenhouse environment at Watsonville, Calif.

Blooming habit: Recurrent.
Bud:
*Size.*—About 4.5 cm long and 3 cm in diameter when the petals start to unfurl.
*Form.*—The bud form is pointed ovoid.
*Color.*—When sepals first divide, bud color is near Red Group 53A. When half blown, the upper sides of the petals are primarily near Red Group 53B; and the lower sides of the petals are primarily Red Group 53C.

*Sepals.*—Color: Upper surface: Near Yellow-Green Group 146B. Lower surface: Near Yellow-Green Group 146C. Length: 3 cm. Width: 1 cm. Shape: Funnel. Surface texture: Smooth. There are five normally appendaged sepals. There are three unappendaged sepals with hairy edges.

*Receptacle.*—Color: Near Yellow Group 144B. Shape: Funnel. Size: About 1 cm long×1 cm wide. Surface: Smooth.

*Peduncle.*—Length: Medium, averaging about 9.5 cm. Surface: Smooth. Color: Near Yellow-Green Group 144B. Strength: Erect, slender.

Blooms:

*Size.*—Medium. Average open diameter is about 9 cm.

*Borne.*—Singly, blooms having rounded shape.

*Stems.*—Strength: Normal. Average length is about 48.5 cm. Diameter: 0.4 cm.

*Form.*—When first open: Cupped. Permanence: Retains its form to the end, flattens, outer petal edges curl slightly.

*Petalage.*—Number of petals under normal conditions: 44.

*Color.*—The upper sides of the petals are near Red Group 45B. The reverse sides of the petals are near Red Group 53C. The base of each petal has thin base color of Yellow-Orange Group 19C. The major color on the upper side is near Red Group 45B.

*Variegations.*—None.

*Discoloration.*—The general tonality at the end of the first day is near Red Group 53A. At the end of the third day is near Red Group 53B.

*Fragrance.*—Slight.

Petals:

*Texture.*—Thin.

*Shape.*—Obovate.

*Surface.*—Smooth.

*Margin.*—Entire. Apex Shape: Round with small point. Base Shape: Obtuse.

*Form.*—Tips slightly recurved.

*Arrangement.*—Imbricated, regularly arranged.

*Petaloids.*—Number: 5. Color: Near Yellow Group 12B and 46B.

*Persistence.*—Petals drop off cleanly before drying.

*Lastingness.*—As a cut flower: Long (about 14 days).

Reproductive parts:

*Stamens.*—Number: 170. Length: 1.0 cm. Anthers: Length: 0.4 cm. Color: Greyed-Orange Group 163B. Arrangement: Regular around styles. Filaments: Color: Near Greyed-Orange Group 182A with Greyed-Orange Group 163C at bottom. Length: 0.5 cm. Pollen: Color: Near Orange-White Group 159A.

*Pistils.*—Number: Many. Length: 1 cm. Styles: Color: Between Greyed-Purple Group 186C and 186D. Length: 0.5 cm. Stigmas: Color: Near Orange-White Group 159A. Length: 0.5 cm.

*Hips.*—None observed.

PLANT

*Form.*—Bush.

*Growth.*—Vigorous, upright.

*Age to maturity.*—1 year.

*Mature plant.*—Height: 3–4 ft. at about one year of age. Width: 3 ft. at about one year of age.

*Rootstock.*—Grafted onto 'Natal Briar' understock.

Foliage: Number of leaflets on normal mid-stem leaves: 5.

*Size.*—Medium (15 cm long×10 cm wide).

*Quantity.*—Normal.

*Color.*—New foliage: Upper side: Near Yellow-Green Group 147A. Lower side: Near Yellow-Green Group 147B. Old foliage: Upper side: Near Yellow-Green Group 147A. Lower side: Near Yellow-Green Group 147B.

Leaflets:

*Size.*—About 7 cm long×5 cm wide.

*Shape.*—Pointed Oval.

*Base shape.*—Rounded.

*Apex shape.*—Pointed.

*Texture.*—Leathery; glossy.

*Edge.*—Serrated.

*Serrations.*—Single, small.

*Petiole.*—Color: Near Greyed-Orange Group 165A. Length: 2.0 cm. Diameter: 0.1 cm.

*Petiole rachis.*—Color: Near Greyed-Orange Group 165A. Underside: Smooth.

*Stipules.*—Length: 1.5 cm, serrated. Color: Near Yellow-green Group 146A.

*Auricle shape, if present.*—Narrow triangle facing outward.

*Disease resistance.*—Resistant to mildew, rust and blackspot under growing conditions in a greenhouse.

*Pest persistence.*—Normal.

*Vein color.*—Near Yellow-Green Group 147C.

*Venation pattern.*—Pinnate.

Wood:

*New wood.*—Color: Near Yellow-Green Group 147A and Yellow-Green Group 147B. Bark: Smooth

*Old wood.*—Color: Near Yellow-Green Group 146B. Bark: Smooth.

Prickles:

*Quantity.*—On main canes from base: None.

Small prickles:

*Quantity.*—On main stalks: None. On laterals: None.

Winter hardiness: Not observed, variety has been grown in greenhouse.

I claim:

1. A new and distinct variety of rose plant of the hybrid tea rose class, substantially as herein shown and described, characterized particularly by big full flower, thornless stem, very shiny leaves and excellent vase life.

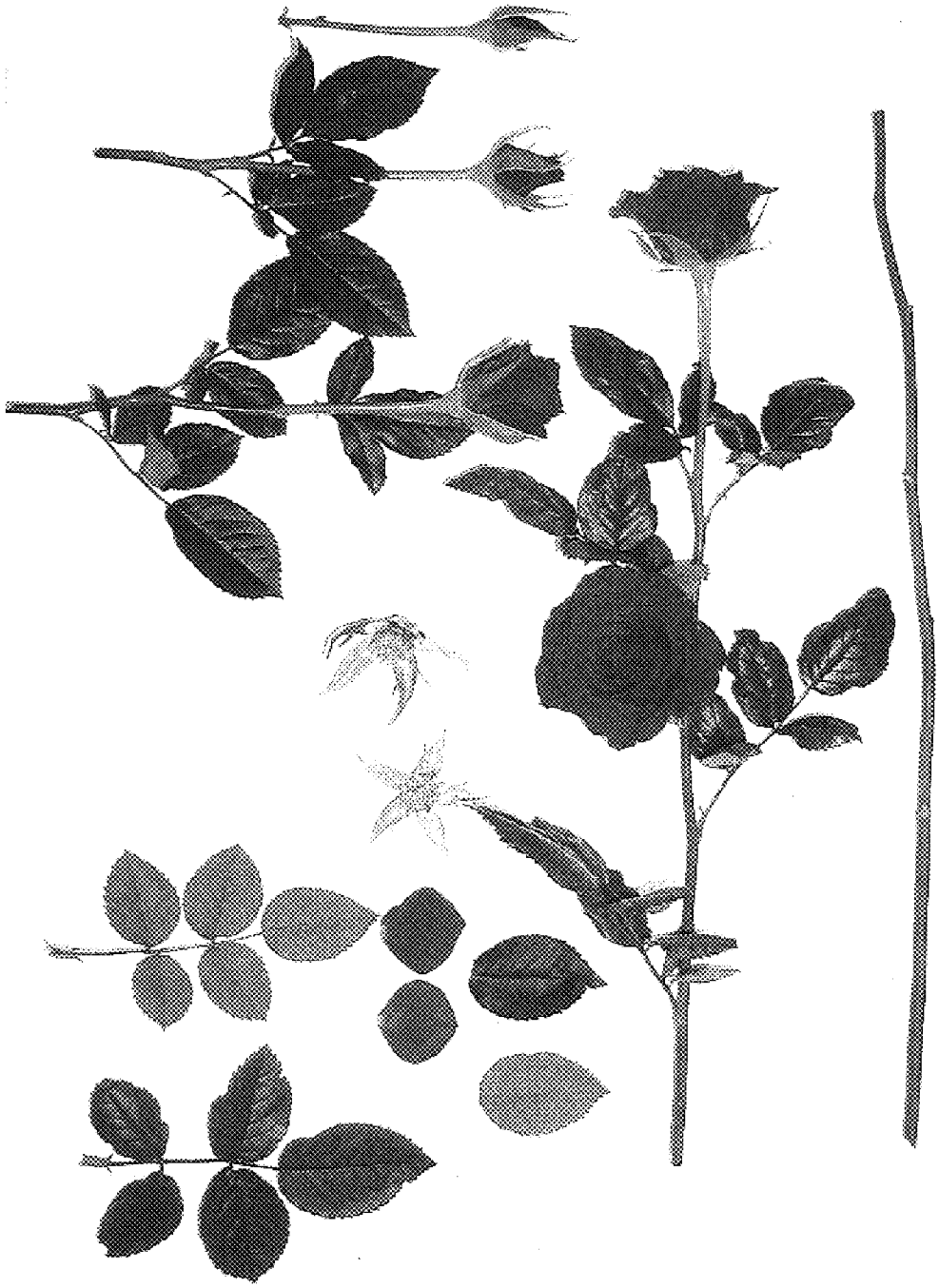

* * * * *